(12) United States Patent
Kutra et al.

(10) Patent No.: US 10,692,208 B2
(45) Date of Patent: Jun. 23, 2020

(54) CHEST WALL ESTIMATION FROM OPTICAL SCANS

(71) Applicant: KONINKLIJKE PHILIPS N.V., Eindhoven (NL)

(72) Inventors: Dominik Benjamin Kutra, Karlsruhe (DE); Thomas Buelow, Grosshansdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 84 days.

(21) Appl. No.: 15/778,939

(22) PCT Filed: Dec. 1, 2016

(86) PCT No.: PCT/EP2016/079514
§ 371 (c)(1),
(2) Date: May 24, 2018

(87) PCT Pub. No.: WO2017/093446
PCT Pub. Date: Jun. 8, 2017

(65) Prior Publication Data
US 2018/0350068 A1 Dec. 6, 2018

(30) Foreign Application Priority Data

Dec. 3, 2015 (EP) ..................................... 15197818

(51) Int. Cl.
*G06T 7/00* (2017.01)
*G16H 50/50* (2018.01)
(Continued)

(52) U.S. Cl.
CPC .............. *G06T 7/0012* (2013.01); *G06T 7/50* (2017.01); *G06T 7/60* (2013.01); *G16H 30/40* (2018.01);
(Continued)

(58) Field of Classification Search
CPC ......... G06T 2207/30068; G06T 7/0012; G06T 7/344; G06T 2207/10081; G06T 7/33;
(Continued)

(56) References Cited

U.S. PATENT DOCUMENTS

2008/0218727 A1 9/2008 Djeziri et al.
2011/0295112 A1* 12/2011 Mordaunt .............. A61B 5/103
600/425

(Continued)

FOREIGN PATENT DOCUMENTS

WO 2009088407 A1 7/2009
WO 2015044184 A1 4/2015

OTHER PUBLICATIONS

Henseler, et al., "Three-dimensional breast assessment by multiple stereophotogrammetry after breast reconstruction with latissimus dorsi flap Phd thesis", Nov. 1, 2011, retrieved from the Internet: URL:http://theses.gla.ac.uk/2981/1/2011Henselerphd.pdf, pp. 1-319.
(Continued)

*Primary Examiner* — Ajibola A Akinyemi (57) ABSTRACT

An image processing system (IPS) includes an input port (IN) for receiving a surface image of an outer layer (OL) of a current biomechanical assembly (TOR). The surface image is acquired by a surface imaging apparatus (DSC) along at least one imaging direction. The assembly includes relative to the imaging direction behind the outer layer, an inner wall (RC) element coupled from behind to the outer layer. The image processing system further includes a wall estimator (WE) configured to provide an estimate for geometrical data of the inner wall element (RC), the estimate being based on image information as per the surface image.

12 Claims, 3 Drawing Sheets

(51) Int. Cl.
*G16H 30/40* (2018.01)
*G06T 7/50* (2017.01)
*G06T 7/60* (2017.01)

(52) U.S. Cl.
CPC ... *G16H 50/50* (2018.01); *G06T 2207/10028* (2013.01); *G06T 2207/30068* (2013.01); *G06T 2207/30088* (2013.01)

(58) Field of Classification Search
CPC . G06T 2207/10072; G06T 2207/10088; G06T 2207/10112; G06T 17/00; G06T 2200/04; G06T 2210/41; G06T 2219/2021; G06T 7/0014; G06T 15/00
USPC .......................................................... 382/128
See application file for complete search history.

(56) References Cited

U.S. PATENT DOCUMENTS

2014/0056502 A1* 2/2014 Twellmann ........... G06T 7/0012
382/131

2015/0182191 A1* 7/2015 Caluser .................. A61B 5/055
600/440

OTHER PUBLICATIONS

Wheat, et al., "Development and assessment of a Microsoft Kinect based system for imaging the breast in three dimensions", Medical Engineering & Physics 36 (2014), pp. 732-738.

Thomson, et al., "Surface Area Measurement of the Female Breast: Phase I. Validation of a Novel Optical Technique", American Society of Plastic Surgeons, www.PRSJournal.com, vol. 123, No. 5, Breast Surface Area, pp. 1588-1596.

Pohlmann, et al., "Breast Volume Measurement Using a Games Console Input Device", IWDM 2014, LNCS 8539, Breast Volume Measurements, pp. 666-673.

Zolfagharnasab, et al, "3D Breast Parametric Model for Surgery Planning—aTechnical Review", 1 Nov. 2013, Retrieved from the Internet:URL:http://www.inescporto.pt/"hfpo/papers/Hooshiar_RECPAD_2013.pdf, 2 pages.

* cited by examiner

CHEST WALL ESTIMATION FROM OPTICAL SCANS

This application is the U.S. National Phase application under 35 U.S.C. § 371 of International Application No. PCT/EP2016/079514, filed on Dec. 1, 2016, which claims the benefit of European Application Serial No. 15197818.6, filed Dec. 3, 2015. These applications are hereby incorporated by reference herein.

FIELD OF THE INVENTION

The invention relates to an image processing system, to an image processing method, to a computer readable medium, and to a computer program element.

BACKGROUND OF THE INVENTION

Breast cancer is the most common cancer type that inflicts women in the western world.
Patients have several treatment options, e.g. surgery, where the affected part of the breast tissue is removed. In the context of joint decision making, biomechanical methods have been developed to simulate the outcome of breast surgery in advance. The simulation provides the patient or medical staff with a visual representation of the surgical outcome to better understand the consequences.

Presently, the production of such simulations of biomechanical assemblies (such as the human torso) is based on MR or CT images acquired for any one of a specific patient. Said differently, before the simulation for a given patient can be computed, imagery of the specific patient needs to be acquired first. However, acquisition of such imagery is either very expensive or constitute in itself health risks due to radiation dosage in case of X-radiation.

SUMMARY OF THE INVENTION

There may therefore be a need for alternative systems or method to facilitate or make safer the production of the simulation of biomechanical assemblies.

It should be noted that the following described aspect of the invention equally applies to the image processing method, the image processing system, to the computer program element and to the computer readable medium. According to a first aspect of the invention there is provided an image processing system, comprising:

an input port for receiving an (input) surface image of an outer layer of a current biomechanical assembly, the image acquired by a surface imaging apparatus along at least one imaging direction, said assembly comprising, relative to said imaging direction behind said outer layer, an inner wall element coupled from behind to said outer layer;

a wall estimator configured to provide an estimate for geometrical data of said inner wall element, said estimate being based on image information as per said surface image.

The estimate of the geometrical data is provided in a suitable data structure such as a polygonal (eg, triangular) mesh model or functionally in terms enveloping functions, etc. The geometrical data includes in particular a description of the shape and/or orientation and/or location of the wall element.

The outer layer essentially occludes the wall element from visual inspection. The proposed method still aims at inferring the geometry of the "underlying" wall element given the geometry of the outer layer as captured by the surface (eg, optical) imaging apparatus. This is possible because in some biomechanical assemblies, the geometry of at least a part of the visible outer layer corresponds to at least one underlying wall element. By "wall element" is meant that part of a potentially larger wall structure that is situated behind the outer layer. In other words, information about the geometry of the underlying wall element can be gathered without using expensive or harmful non-surface (that is, penetrative) imaging equipment such as MRI or CT. Optical imaging is sufficient for present purposes. More specifically, and in one non-limiting embodiment, the biomechanical assembly is a human (eg female) torso. The skin defines the outer layer which occludes that part of the rib cage that sits behind one or both breast. By "shape" of the wall element is meant, in one embodiment, the geometrical envelope formed by the ribs situated behind one or both breasts. As a refinement of this, the wall element may define instead the inner boundary formed by the rib cage and the overlaying pectoral muscle. In yet other embodiments, the wall elements relates only to the pectoral muscle wall overlaying the ribs. The proposed system can be applied to other parts of the human or animal anatomy occluded by skin.

The geometrical data provided by the proposed system can be used with benefit in biomechanical simulations. In biomechanical simulations of the breast, it is preferable to know both, the shape and location of the posterior boundary, that is, of that part of the rib cage to which the breast tissue is coupled.

According to one embodiment, said outer layer includes a bulged portion and the system further comprises an image analyzer configured to analyze the surface image into a (first) partial image that represents said bulged portion wherein the wall estimator is configured to provide said estimate whilst ignoring image information as per said partial image. Put differently, the complement of said first partial image forms a remainder part (remainder image) of the input image and the estimate is based only on this remainder image with image information in the first partial image being ignored. In one embodiment, this wall estimate is obtained by fitting a geometrical model ("primitive") to only the remainder part of the input surface image. This geometrical model is a "primitive" in the sense that its overall shape type corresponds to the shape circumscribed by the input surface image. In the female human torso embodiment, the bulged portion corresponds to the breast tissue. This approach takes advantage of the fact that part of the skin contour corresponds at least in shape (but not necessarily in location) to the rib cage wall shape, if one ignores the "distortive" effect, as it were, of the breast geometry.

In order to improve this shape estimate and/or to estimate the location of the wall element inside the torso, the system includes, according to one embodiment, a thickness estimator is configured to provide an estimate for a thickness of an inner layer of or within said assembly. The inner layer is situated between said inner wall and said outer layer. The wall estimator is configured to combine said thickness estimate with the image information as per said surface image to so provide said geometrical data of said inner wall element. In the female human torso embodiment, the bulged portion corresponds to the breast tissue and the inner layer is a layer of connective tissue between rib cage and skin/breasts. The thickness estimate may be supplied in form of an average thickness, thickness at single control point or, preferably, as thickness values at a plurality of control points, those readings together forming a thickness profile. Applicant discovered that knowledge of the thickness profile of this layer allows refining the geometrical data of the rib cage element gained by fitting the geometrical primitive to the remainder surface mentioned above. Also, knowledge of this thickness profile and the incorporation of this geometrical information into the simulation allows building yet more realistic simulations of the torso as this layer has been found to affect breast dynamics under gravity.

According to one embodiment said thickness estimator operates based on a functional relationship model previously learned from ground truth data and historical metadata taken from a population of different types of such biomechanical assemblies. Machine learning or more traditional function fitting techniques can be used. This allows accurate and cost effective thickness estimation.

According to one embodiment the thickness estimator operates to apply metadata of the current biomechanical assembly to the learned functional relationship model to so obtain the thickness estimate for the current biomechanical assembly. This allows applying the learned knowledge to the particulars of a specific patient.

According to one embodiment, the system comprises a simulation unit configured to generate a biomechanical simulation of said assembly. The simulation may be rendered graphically.

According to one embodiment said imaging apparatus includes a depth sensing camera. Other optical techniques such as stereo-imaging, laser scanner systems (with or without time-of-flight) are also envisaged as are non-optical techniques such as echolocation or others, although optical systems are preferred because of their higher accuracy. In short, and according to one embodiment, a system and related method is proposed that enables the biomechanical simulation of the breast without the need for MR or CT imaging, purely based on a representation of the surface of the object which can be gained in one preferred embodiment from optical surface scans and metadata.

BRIEF DESCRIPTION OF THE DRAWINGS

Exemplary embodiments of the invention will now be described with reference to the following drawings wherein.

DETAILED DESCRIPTION OF EMBODIMENTS

What is proposed herein is an image processing system IPS that estimates, based on surface image data of a biomechanical assembly, the geometry of internal structures within said assembly occluded from view by an outer layer of said assembly. In particular, the geometry of a wall structure within the assembly is estimated.

Figure 1:
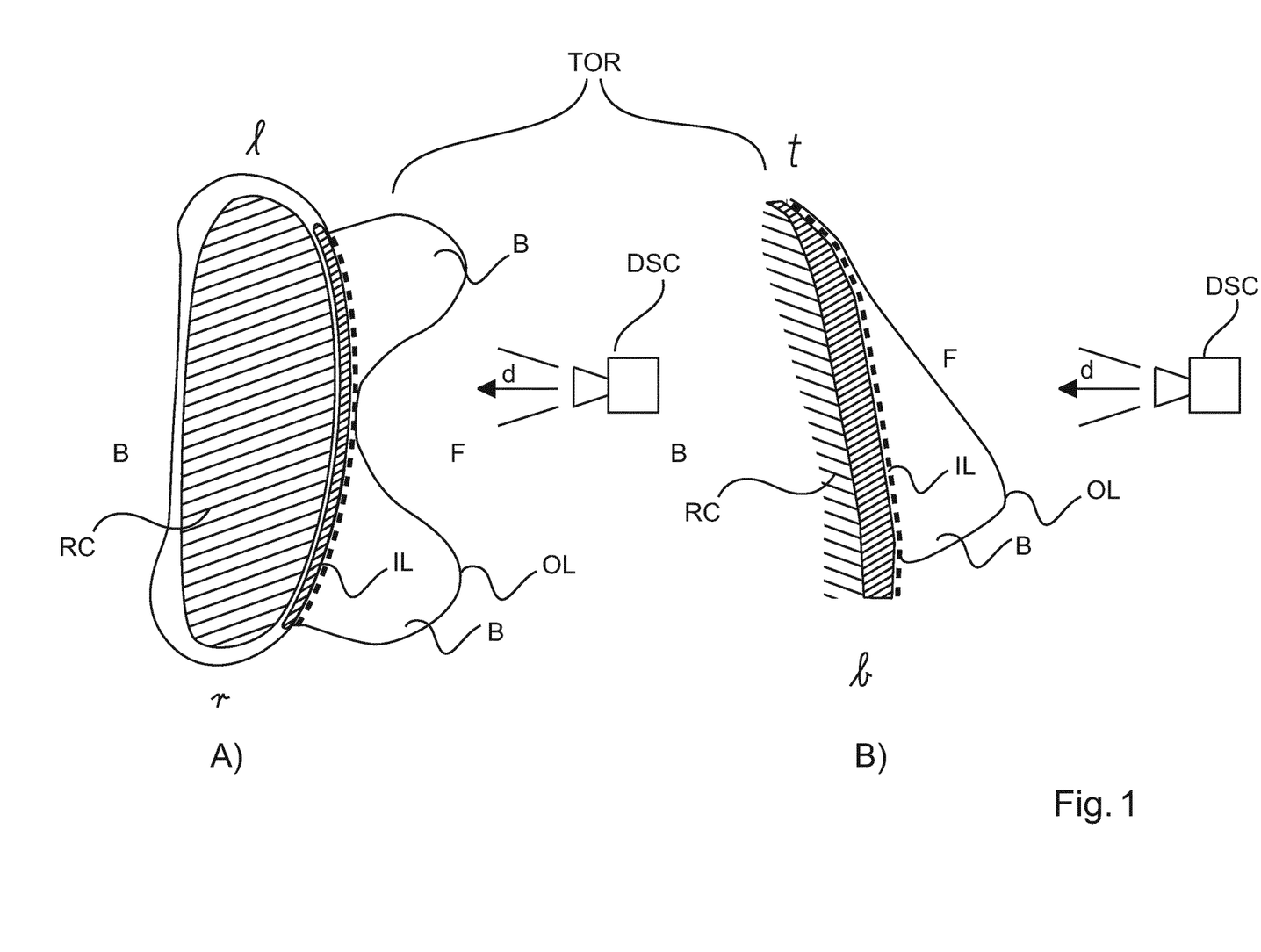
FIG. 1, which is not necessarily to scale, shows components of a biomechanical assembly.

But before explaining operation of this image processing system in more details, it will be beneficial to refer first to FIG. 1 (which is not necessarily to scale) to illustrate basic components of a biomechanical assembly TOR.

FIG. 1A shows an axial view of a biomechanical assembly, such as a female human torso TOR. FIG. 1B on the other hand affords a sagittal view (side elevation) of said torso TOR. In FIGS. 1A, B, the reference character l and r indicate left and right, respectively, whereas reference characters t and b refer to, respectively, top and bottom portions of torso TOR. Structurally speaking, the torso TOR has a layered composition, one layer arranged behind the other, with the exposed outer layer OL, the skin that is, occluding the layers within the torso TOR. The two breasts are formed as bulged portions of the skin OL caused by the underlying breast tissue bulging into the skin OL. The breast tissue couples to a portion of the rib cage RC within the torso. It is in particular this portion which is referred to herein as the rib cage wall element RC, or simply the "wall element". More particularly, the breast tissue is coupled to the rib cage wall element. The wall element RC is a mix of a bone (ribs) and pectoral muscle tissue. There is also a further, intermediate or inner layer IL between skin/breast tissue and the wall element. This inner layer IL is formed from connective tissue, but also breast tissue and fat tissue. The main components of the female torso looked at as biomechanical assembly includes thus the outer layer (skin), the underlying breast tissue, the rib cage RC which forms a wall to which the breast tissue is coupled to via the intermediate layer situated between breast tissue and the rib cage.

One goal as envisaged in the present application includes acquiring one or more surface images by an optical camera DSC of the skin OL and we wish to infer, based inter alia on this surface imagery, the geometry of the remaining, underlying components of the torso, in particular, we wish to ascertain geometrical data about the rib cage wall to which the breasts are coupled via the intermediate layer IL. The geometrical data includes geometrical description that describes in particular the shape of the rib cage wall, in particular, of that part of the rib cage wall to which the breast tissue is coupled. In addition or instead, the geometrical data may also include position and/or orientation at one or more control points of the rib cage wall. In one embodiment it is envisaged herein to use the geometrical data about the rib cage wall RC to furnish a biomechanical simulation of the torso subject to forces, in particular subject to gravity.

In order to achieve a particularly realistic biomechanical simulation of the torso, it is advantageous to also have geometrical data of the inner or intermediate layer IL available. The inner layer IL effectively surrounds or embeds that part of the breast tissue that connects to the rib cage. Knowledge of the shape and/or in particular the thickness of this inner layer has been observed by applicant to lead to highly realistic biomechanical simulations. It has been found furthermore that the thickness estimation of the inner layer can be based on prior knowledge learned from a population of torsi. In other words and in summary, based on the surface image of the skin OL and based on prior knowledge about the average thickness of the inner layer (which can be related via metadata to the actual patient from which the surface imagery is collected), geometrical data for each of the above-mentioned components is established. In particular, geometrical data for the inner layer and the chest wall is computed.

The geometrical data for the various components, in particular chest wall RC and inner layer IL, can then be virtually linked together at virtual linkage points which encode the elasticity characteristics of the respective materials (tissues) which are generally known. The so linked data structure can then be used as an input for a simulation program which can render for instance a graphical simulation of the whole torso. Based on the simulation, the overall appearance of the torso can be studied under the influence of gravity, and when certain tissue elements from the breast are removed such as in a mastectomy or other operative interventions where tissue portions are removed. For instance, in the event cancerous tissue has been detected in the breast, it is generally an excision volume (eg, a cylinder) of tissue around the cancerous site which is removed from the breast. The surgeon or interventionist can then choose the optimal orientation for this excision volume so as to achieve the most favourable visual appearance, under gravity, for the patient. Although envisaged herein as the preferred embodiment, it will be understood that the human female torso is merely one embodiment of the biomechanical assembly. That is, the proposed imaging processing system may also be applied with benefit to other parts of the human (or animal) anatomy. The dashed line in FIG. 1 shows the particular shape of the rib cage wall element one wishes to estimate.

Figure 2:
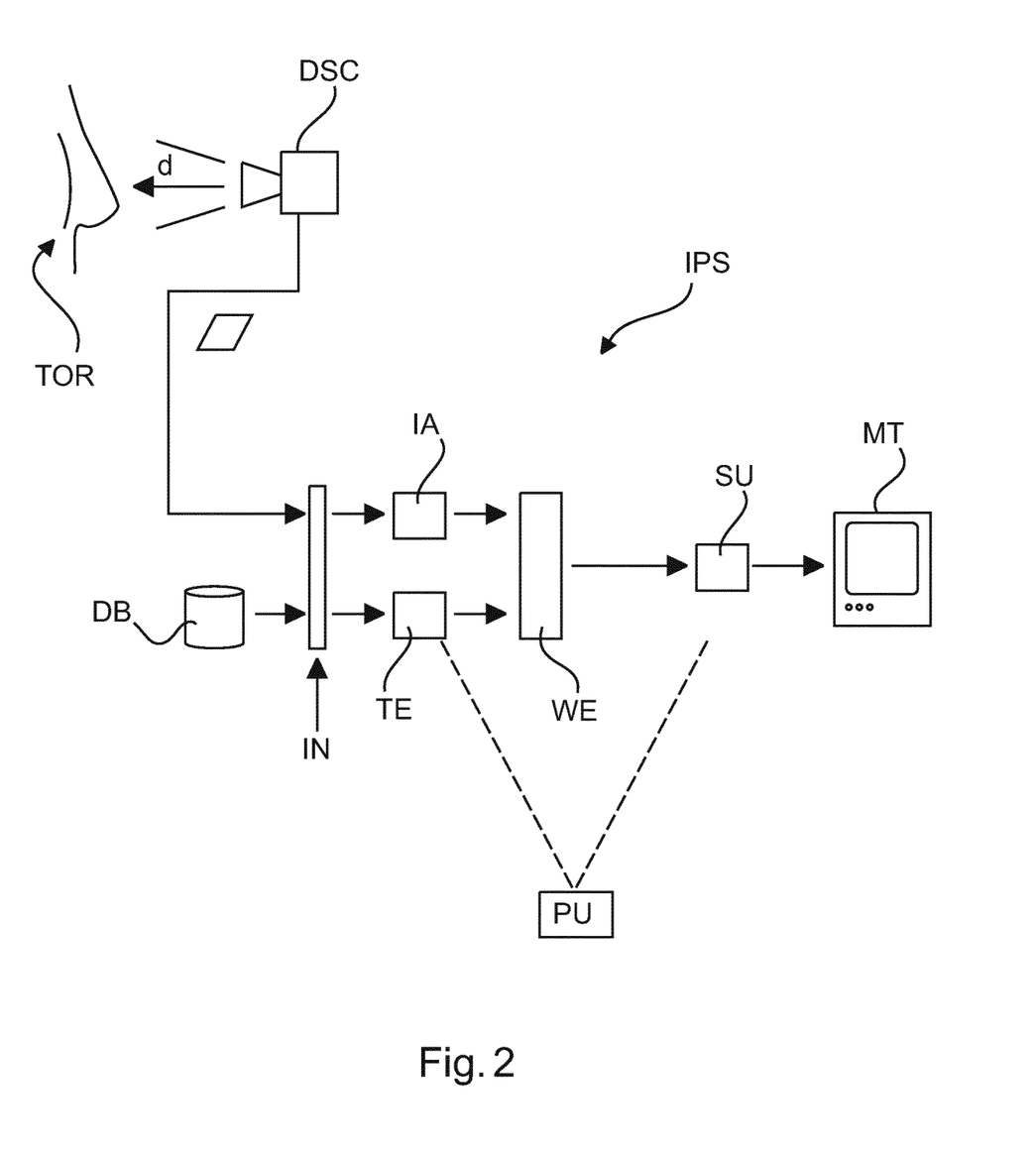
FIG. 2 shows a schematic block diagram of an image processing system.

Reference is now made to FIG. 2, where a schematic block diagram of the proposed image processing system IPS is shown. The image processing system includes the surface camera DSC, such as a depth sensing camera, for instance Microsoft Kinect, and a plurality of processing components that can be implemented as software modules on a general purpose computing unit PU. In alternate embodiments, the modules of the IPS in FIG. 2 are arranged in a distributed architecture and connected in a suitable communication network. The modules may be arranged in hardware as suitably programmed FPGAs (field-programmable gate array) or as hardwired integrated circuits.

The (one or more) input surface image, acquired along a (one or more) imaging direction(s) d, is received at input port IN of system IPS. The one or more images preferably encode spatial depth information. Based inter alia on this (one or more) input image, the wall estimator WE estimates geometrical data for the underlying rib cage wall occluded by the skin OL and the inner tissue IL. The geometrical data includes in particular shape information but may in addition or instead include position and/or orientation.

To achieve this estimate and according to one embodiment, the system IPS includes an image analyser IA. The wall estimator WE operates in conjunction with the image analyser IA. The image analyser analyses the surface image into two partial images: i) one partial image, the bulged portions of the image surface that represents the two breasts, referred to herein as the breast image and ii) a second partial image, that is, the non-bulged part of the surface image, that represents the remainder of the skin that surrounds the breast portions. The second part will be referred to herein as the remainder image. The remainder image is may be assumed to follow, in a first approximation, more closely the course and shape of the underlying rib cage wall. A primitive 3D model of the torso, such as a super-ellipsoid or other, is then fitted by the wall estimator WE to only said remainder surface image. That is, image information as per the bulged surface portions of the input image are essentially ignored during this fitting operation. In other words, the estimator WE carries out this first torso fitting operation to arrive at a model of how the torso TOR may look like if there were no breasts. That is not to say that the image information as per the breast image is discarded. Rather, and as will be explained in more detail below, the breast image is retained and used to build up the simulation. More specifically, and in one non-limiting embodiment, the isolated breast images are themselves converted into separate mesh models, one for each breast, and are then later linked up with the chest wall model when building the simulation. It should be understood that the proposed system and method may not necessarily be applied to both breasts, may be applied only to the breast which is to undergo the surgery.

The fitted primitive (that is, an initial shape type), which may be implemented as a mesh structure, can be regarded as a first estimate for the geometrical data, in particular for the shape, of the wall element RC. In other words, in this simplified modelling, a "zero" thickness of the inner layer is assumed.

Preferably, however, to achieve superior simulation quality, the image processing system IPS further includes as an additional processing component, a thickness estimator TE, which is configured to estimate the thickness of the inner layer situated between the skin/breast and the inner rib cage wall RC. The tissue estimator uses prior knowledge to furnish for instance an estimate for the average thickness of the inner layer IL along the course of the rib cage wall RC. In another embodiment, the thickness estimator furnishes a plurality of thickness readings at predefined control points along the chest wall. The prior knowledge is held in suitable form (tables, algorithmically, etc.) in a knowledge database DB and can be queried therefrom by thickness estimator TE. Estimating the thickness of this inner layer also allows localizing the inner wall, specifically, estimating how "deep" inside the torso the inner wall is located.

The i) geometrical data description of the inner layer and ii) the estimated geometrical data of the wall as per the geometrical model fitted to the remainder surface may then be combined to achieve an even better estimate of the wall. For instance, the thickness estimate can be subtracted from the previous estimate of the geometrical torso model (with breast geometry excluded) to so refine the estimate of the rib cage wall shape and/or location and/or orientation. In other words, knowledge about the thickness of the inner layer allows refining the fitted geometrical torso model to pinpoint more exactly location and shape of the rib cage wall (illustrated as the dashed line in FIG. 1).

The geometrical data (eg, mesh models) for the breast image(s), for the chest wall RC and/or for the inner layer are then forwarded to a simulation unit SU. In particular, the geometrical data of the so refined wall shape and the thickness of the inner layer can be linked up together with the meshes for the breast image by the simulation unit SU to achieve a better, more realistic simulation of the complete torso. The simulation unit renders a graphical simulation of the dynamics of the Torso given a specification of forces, such as gravity, to which the torso TOR is assumed subjected to.

If a graphical presentation of the simulation is desired, this can then be displayed on a display device such as computer monitor MT. The proposed image processing system IPS is arranged as an interactive system. In other words, the user can manipulate the geometrical data and the simulation is then rerun in response to such a manipulation to update the simulation, preferably in quasi-real-time, whilst the geometrical data is being manipulated. More specifically, the simulation is embedded in suitable GUI architecture comprising event handlers that monitor a user's interaction with the currently displayed simulation. The user may use input means such as pointer tools (mouse, stylus) or touch screen interaction to change the geometrical data. In this manner a virtual surgical intervention can be simulated where breast tissue is excised and the system IPS responds by a graphical rendering of the simulation of the now changed dynamics of the torso. The user can hence find the most favourable way of removing the tissue to maintain as much as possible the natural dynamics of the torso thus promoting a better quality of life for the patient post-surgery.

Although a graphical representation of the biomechanical simulation, as described above is the preferred embodiment, a purely numerical simulation may be sufficient in some instances and such embodiments are also envisaged herein.

Figure 3:
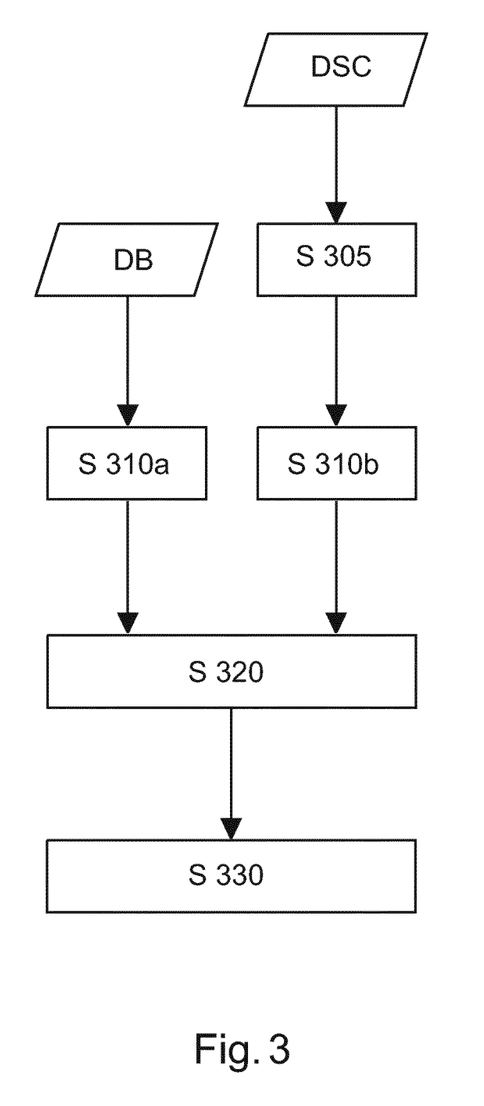
FIG. 3 shows a flow chart of an image processing method.

Reference is now made to FIG. 3, where a flow chart is shown for an image processing method underlying operation of the image processing system in FIG. 2. However, it will be understood by those skilled in the art that the following description of the method can also be read in isolation and is not necessarily tied to the architecture described in FIG. 2.

At step S305, the input surface image of the biomechanical assembly, such as a human or animal torso, is received. The surface image may be constituted as a point cloud of measured distances that together define the shape or course of the skin that envelops the underlying layers. The surface image is acquired along one or more imaging directions by preferably a surface imaging apparatus DSC such as a depth sensing camera or other optical, in particular non-ionizing imaging techniques. Structurally, as illustrated in FIG. 1, the biomechanical assembly TOR is thought to comprise the outer layer OT visible to the camera DSC and, occluded therefrom along the imaging direction, an inner layer IL and a wall element. The inner layer is situated between the outer layer and the wall element which is coupled to the inner layer from behind (away from the camera position). In other words, the wall element is coupled to the outer layer via the inner layer.

At step S320, geometrical data that describe the wall element is estimated. In one embodiment, this estimation is based on an intermediate step S310a where the surface image is analyzed into the two partial images mentioned above: the breast image, which describes or represents the one or more bulged portions such as breast tissue of a female torso, and the remainder image that represents the course of the skin outside the breast portions. A geometrical model, a primitive (such as a super-ellipsoid or other shape) is then fitted only to the remainder image. The breast image on the other hand is, for now, ignored in this fitting operation. In this embodiment, the step of estimating the geometry of the wall RC is based only on image information as per the remainder image. In other words, the bulged portions in the breast image are ignored so as to arrive at a first estimate for the geometrical data of the wall element. The choice of shape for the primitive will depend on the expected over-all shape characteristic of the anatomy of interest and shapes other than the mentioned super-ellipsoid may be called for if it is not the human torso that is under consideration.

The exclusion of breast image information for the purpose of fitting the geometrical model can be achieved in different ways. For instance, in one embodiment, artificial markers are used that form easily recognizable artificial "landmarks". These markers (stickers, tabs, etc.) are manually attached (for instance by adhesion) to the patient's skin before acquisition of the surface image. The markers are arranged circumferentially around to the breast(s). The marker footprints may then be automatically detected by a segmentation operation to so distinguish between the breast image and the non-breast, remainder image. Alternatively, the breast portions are automatically detected in a 3D reconstructed mesh without using artificial markers. Model based approaches could be used to identify the parts of the skin that belong to the breast. Such models could be trained on 3D scans of a population.

By appropriate interpolation based on these (natural or artificial) landmarks using a "sheet"-like interpolation function, the breast image information can be eliminated. Specifically, the image information representative of the breast is replaced through interpolation with an interpolation surface of lesser curvature, interpolated from edges of the remainder surface image. Yet more specifically, a curve can be fitted to the plurality of marker points identified in the input surface image. This operation then leaves one or more "holes" in the surface image, with the holes outlined by the curve and the curve thus defining the edge(s) of the remainder surface. It is then the surfaces of the fitted primitive (such as the ellipsoidal model surface) that replaces the breast image part to so arrive at a first geometrical estimate for the shape or course of the wall.

In addition or instead of said step S310a of analyzing the surface image into the two partial images and the fitting of the geometrical model to the remainder image, there is a step S310b where a thickness of the inner layer is estimated from prior knowledge from other anatomies of the same type. The so estimated thickness is then applied to the fitted geometrical model to derive a mode refined estimate for the wall element.

More specifically, the thickness estimation step is based on a previous learning step where a dependency relationship between historical metadata and characteristics of the inner layer thickness was learned from ground truth data. The ground truth data comprises for instance previously acquired MRI or CT images from a population of female patients. The historical metadata includes for instance parameters such as age, weight, BMI, patient torso dimension in lateral direction (from left to right), and other factors (or different combination of any of these factors) that describe the individuals in the population. The metadata are referred to herein as "historical" because it relates to image data previously collected from a population.

The ground truth materials such as the MRI images are assumed to represent in sufficient contrast the three structures of interest, namely the rib cage, the wall and the inner layer. The ground truth imagery is then automatically or manually processed to measure the relative distances between the rib cage wall and the inner layer at a single control point or at a plurality of predefined (not necessarily equidistant) control points distributed along the wall RC. These measurements together with the metadata of those ground truth data are then fed into a machine learning algorithm such as a Random Forest (see for instance, A. Criminisi et al in "Decision Forests for Classification, Regression, Density Estimation, Manifold Learning and Semi-Supervised Learning", No. MSR-TR-2011-114, 28 Oct. 2011, neural networks or other to learn the functional relationship (a "trained model" that is) between metadata and the tissue thicknesses. Once trained on a sufficient corpus of ground truth data, the model can then be fed with any specification for metadata and the trained model will output values which can be taken as estimates for the layer thickness of wall versus layer distance.

This thickness estimation operation may also be achieved by using more traditional function fitting procedures. In this approach, a parameterized functional description for the, as yet unknown, metadata-versus-layer-thickness dependency is assumed given. For instance, one may use a certain class of functions, such as a high-dimensional polynomial with the coefficients being the parameters to be fitted. The specific values for these parameters are then "learned" by fitting the known historical metadata in an optimization procedure to the known thickness/distance measurements using the assumed functional description (the polynomial for instance) to compute "optimal" parameters based on some optimization criteria such as least square sums, etc. Once the parameters are computed, these can be substituted as parameters into the assumed functional description which now provides a "rule" or "formula" to compute, for any specification of metadata, the inner layer IL thickness/distance to rib cage wall. One example for such an optimization procedure for revealing such a-priori unknown relationships/ dependencies is the "Response Surface Methodology" (RSM) from the field of experimental design in statistics.

See for instance G Box and al in "On the Experimental Attainment of Optimum Conditions", Journal of the Royal Statistical Society, Series B (Methodological), Vol. 13, No. 1, (1951), pp 1-45.

In other words, the thickness of the inner layer can be estimated from prior ground truth data in a traditional function fitting approach or in via machine learning. The earlier leads to an explicit form of the metadata-versus-layer dependency and could be obtained from a single meta-data and ground truth image set. The other option is to first average the ground truth data set and the metadata and to then apply the fitting operation to the average data set.

Machine learning approaches as outlined above have the advantage that the dependencies can be learned at once from a plurality of ground truth image data sets and their associated historical metadata. No collapsing the multiple data sets by averaging is required. In the machine learning approach the output does not usually provide an explicit functional description or "formula" for the dependency as does the more traditional function fitting approach. Instead, in machine learning the "learned" dependency is encoded in the individual and mutual configurations of the plurality of decision tree structures of the random forest or, in case of neural networks, in the configuration of the node layers of the neural network.

The learning or fitting operation as described above is done in a precursor phase prior to the above-mentioned step of estimating the thickness of the inner layer IL for a given patient. All that is required for the thickness estimation step is to merely provide the specific metadata of the particular patient for which the simulation is to be drawn up so as to arrive at the thickness estimate. In yet other words, an ad-hoc MRI or CT image for the given patient can be avoided because one can use as ground truth the corpus of all suitable imagery already acquired for other patients in the past. This existing corpus of ground truth imagery could be collected from image storage system (PACS) attached to HIS systems. More particularly and to be clear, the ground truth imagery (for instance the MRI or CT images) used for learning the functional relationship is not image data acquired from the specific patient for which the simulation is to be run (although such personal imagery can still be acquired or used of course if necessary).

The functional metadata versus tissue thickness relationship learned can be stored in suitable data structure in the knowledge database DB. Suitable data structures include tables, functional/algorithmic descriptions or others. The application of the current metadata of the current patient whose torso geometry is to be learned can be as simple as a database query and a look-up operation against the known thickness versus metadata dependencies. In other embodiments, this query operation involves computations such as interpolating the desired thickness from known metadata-versus-thickness pairs/tuples. In yet other embodiments, the metadata are applied to fill "place-holder" positions in the learned functional description (which is essentially a mathematical formula). Arithmetical operations as prescribed by this functional description are then performed for the required number of control points to derive the one or more thickness estimates for these control points. These one or more thickness readings are then applied to the geometrical model fitted in step S310a to so derive a refined estimate for the shape/location/orientation of the rib cage wall RC. At step S330, the geometrical data for the inner layer and that for the wall element is combined to form a biomechanical simulation of the biomechanical assembly.

More specifically, in one embodiment, the geometrical data estimated for the rib cage wall and inner layer are provided in form of computer graphic meshes. These meshes are combined at linkage points with meshes for the one (or both) breast tissues portions from the input surface image, previously ignored at step S310a. Just like the nodes of the mesh, it is also the linkage points between those meshes that encode elastic properties of the materials which these meshes represent. And because the material composition and the density of the torso tissues are known, a dynamical simulation of the whole torso structure under the influence of any force (eg, gravity) can be computed by solving a system of partial differential equations (PDEs), using the provided geometrical data as boundary conditions.

In one embodiment, the simulation is displayed on a display unit, either in isolation or is displayed alongside the original surface scan image as recorded by the camera DSC.

In sum, what is proposed herein, in one embodiment, is a method that enables the biomechanical simulation of the breast without the need for MR or CT imaging, purely based on optical surface scans and meta-data. Using three-dimensional surface data that can be acquired cost-effectively, e.g. with a depth sense camera, we propose to estimate the shape of the chest wall and therefore the tissue between surface and chest wall by using, in first step, a geometric model that is fitted to the image date of the surface of torso (with image information on the actual breast tissue excluded from this fitting). Tissue thickness estimation is then metadata driven and is estimated in a second step and this can be used to refine the geometrical model obtained in the first step.

It should be noted that the above described method and system can be applied to more than one inner wall element. For instance, the method and system described above may be refined by estimating, respectively, the rib cage and the overlaying wall of the pectoral muscle as two discrete wall elements, each estimated separately as a structure on its own. This can approach be even extended to more complex assemblies with more than two (overlaying) wall elements. The simulation is then able to capture the dynamics of two or more such wall elements interconnected, thus allowing one to achieve an even higher level of realism.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
an input port for receiving a surface image of an outer layer of a current biomechanical assembly wherein the biomechanical assembly includes a human torso, the surface image acquired by a surface imaging apparatus along at least one imaging direction, wherein the biomechanical assembly comprises, relative to the imaging direction behind the outer layer, at least one inner wall element coupled from behind to the outer layer, wherein the surface image is a surface image of a human torso acquired by a depth sensing camera;
a wall estimator configured to provide an estimate for geometrical data of the inner wall element, the estimate being based on image information as per the surface image, wherein the outer layer comprises a bulged portion;
an image analyzer configured to analyze the surface image into a partial image that represents the bulged portion, wherein the wall estimator is configured to provide the estimate while ignoring image information as per the partial image and fit a 3D primitive model of the human torso image surface without the partial image;
a thickness estimator configured to provide an estimate for a thickness of an inner layer of the biomechanical assembly, the inner layer being situated between the inner wall element and the outer layer, wherein the thickness of the inner layer is estimated based by trained models based on previously determined data or databases of three-dimensional torso images of other patients.

2. The system of claim 1, wherein the thickness estimator operates based on a functional relationship model previously learned from ground truth data and historical metadata taken from a population of different types of such biomechanical assemblies.

3. The system of claim 1, wherein the thickness estimator is configured to combine the thickness estimate with the image information to provide geometrical data of the inner wall element.

4. The system of claim 3, wherein the thickness estimator is configured to apply metadata of a current biomechanical assembly to the learned functional relationship model to obtain the thickness estimate for the current biomechanical assembly.

5. The system of claim 1, further comprising simulation unit configured to generate a biomechanical simulation of said the biomechanical assembly.

6. The system of claim 1, further comprising the imaging apparatus and/or a display unit.

7. The system of claim 1, wherein the geometrical data comprises at least one of: a shape and a location description of the inner wall element.

8. A method of image processing, comprising:
receiving a surface image of an outer layer of a current biomechanical assembly of a current subject, the surface image having been acquired via a surface an optical depth sensing camera and along at least one imaging direction, wherein the biomechanical assembly comprises, relative to the imaging direction behind the outer layer, an inner wall element coupled from behind to the outer layer by an inner layer;
providing an estimate for geometrical data of the inner wall element based on image information as per the surface image, wherein the outer layer comprises a bulged portion, and wherein the estimate is determined by analyzing the surface image via a partial image that represents the bulged portion, and wherein, in providing of the estimate, image information as per the partial image is ignored;
fitting a primitive 3D model to the surface image with the partial image ignored; and
estimating a thickness of the inner layer of the biomechanical assembly of the current subject using models trained based on data from 3D diagnostic images of the biomechanical assemblies of a population of previous subjects.

9. The method of claim 8, further comprising:
providing an estimate for a thickness of the inner layer of the biomechanical assembly of the current subject, wherein the inner layer is situated between the inner wall element and the outer layer, and further including combining the thickness estimate with surface image information of the current subject to so provide the geometrical data of the inner wall element of the current subject.

10. The method of claim 8, further comprising:
generating a biomechanical simulation of said biomechanical assembly.

11. A non-transitory computer readable medium comprising computer code that when executed by a processing unit causes the processing unit to perform steps comprising:
receiving a surface image of an outer layer of a biomechanical assembly of a current subject, wherein the surface image is acquired via an optical depth sensing apparatus along at least one imaging direction, and wherein the biomechanical assembly comprises, relative to the imaging direction behind the outer layer, an inner wall element coupled by an inner layer behind to the outer layer, the outer layer including a bulged portion; and
determining an estimate for geometrical data of the inner wall element based on image information as per the surface image by:
fitting a geometric primitive to the surface image ignoring the bulged portion,
estimating a thickness profile of the inner layer based on historical 3D images of biomechanical assemblies of a population of prior patients,
from the fit geometric primitive and the thickness profile of the inner layer, estimating a shape of the inner wall element.

12. An image processing system comprising:
an optical depth sensing camera configured to generate a surface image of an outer surface of the skin of a human torso which human torso has an inner layer disposed between the skin and a rib cage wall, the inner layer being disposed behind the outer surface in a viewing direction and occluded from the depth sensing camera in the viewing direction of the depth sensing camera, the outer surface of the human torso including a breast portion;
one or more computer processors configured to:
fit a geometric primitive to a non-breast portion of the surface image to generate a first estimate of a shape and course of the rib cage wall assuming an inner layer of a zero thickness,
estimating a thickness profile of the inner layer based on historical metadata from three-dimensional images of human torsos of a population of other human patients,
from the first estimate of the shape and course of the rib cage wall assuming an inner layer of zero thickness and the estimated thickness profile of the inner layer, generating a second estimate of the shape and course of the rib cage wall.

* * * * *